United States Patent
Hiraoka et al.

(10) Patent No.: US 6,589,754 B1
(45) Date of Patent: Jul. 8, 2003

(54) IMMUNOASSAY ELEMENT AND PROCESS FOR IMMUNOASSAY

(75) Inventors: Toshikage Hiraoka, Saitama (JP); Tetsuji Tanimoto, Tokyo (JP); Yoshihiko Makino, Asaka (JP); Tadashi Ninomiya, Tokyo (JP); Hiroshi Shinoki, Asaka (JP); Yoshihiro Ashihara, Tokyo (JP); Naofumi Hora, Asaka (JP); Masashi Ogawa, Asaka (JP)

(73) Assignees: Fuji Photo Film Co., Ltd., Kanagawa (JP); Fujirebio Inc., Tokyo (JP)

( * ) Notice: Subject to any disclaimer, the term of this patent is extended or adjusted under 35 U.S.C. 154(b) by 1254 days.

(21) Appl. No.: 08/946,685

(22) Filed: Oct. 8, 1997

Related U.S. Application Data

(63) Continuation of application No. 08/520,768, filed on Aug. 30, 1995, now abandoned, which is a continuation of application No. 08/163,734, filed on Dec. 6, 1993, now abandoned, which is a continuation of application No. 07/763,198, filed on Sep. 20, 1991, now abandoned.

(30) Foreign Application Priority Data

Sep. 20, 1990 (JP) ............................................. 2-248711

(51) Int. Cl.$^7$ ............................................. G01N 33/53
(52) U.S. Cl. .................. 435/7.92; 422/56; 422/60; 422/68.1; 422/101; 435/7.1; 435/7.9; 435/7.91; 435/7.93; 435/22; 435/188; 435/196; 436/518; 436/514; 436/529; 436/170

(58) Field of Search .......................... 422/56, 60, 68.1, 422/101; 435/7.1, 7.9, 7.91, 7.92, 7.93, 22, 188, 196; 436/518, 514, 529, 170

(56) References Cited

U.S. PATENT DOCUMENTS

| 4,066,509 A | * | 1/1978 | Ceska | 195/103.5 R |
| 4,089,747 A | * | 5/1978 | Bruschi | 195/99 |
| 4,595,655 A | * | 6/1986 | Self | 435/7 |
| 5,093,081 A | * | 3/1992 | Sudo et al. | 422/56 |

OTHER PUBLICATIONS

Nakamura et al "Enzyme Immunoassays: Heterogeneous and Homogeneous Systems" in *Vol. I: Immunochemistry* D.M. Weir ed 1986 pp 27.1–27.20 Blackwell Scientific Publications.*

Tietz, N.W. ed, 1986 *Textbook of Clinical Chemistry* W.B. Saunders Company, pp 729–734.*

* cited by examiner

*Primary Examiner*—Bao-Thuy L. Nguyen
(74) *Attorney, Agent, or Firm*—Reed Smith LLP

(57) ABSTRACT

An immunoassay element for quantitatively analyzing a macromolecular antigen by determining the change in enzymatic activity caused by a reaction between the macromolecular polymer antigen and an enzyme-labelled antibody. The immunoassay element comprises a substrate layer containing a non-diffusible substrate which forms a diffusible material in the presence of the enzyme, and a reagent layer containing a fragmenting enzyme for further fragmenting the diffusible material into a lower molecular weight product. Also provided is a process for quantitatively analyzing a macromolecular antigen in a sample by the use of the immunoassay element.

24 Claims, 2 Drawing Sheets

CRP (mg/dl)

CRP (mg/dl)

IMMUNOASSAY ELEMENT AND PROCESS FOR IMMUNOASSAY

This is a continuation of application Ser. No. 08/520,768, filed Aug. 30, 1995, now abandoned, which in turn, is a continuation of application Ser. No. 08/163,734, filed Dec. 6, 1993, now abandoned, which, in turn, is a continuation of application Ser. No. 07/763,198, filed Sep. 20, 1991, now abandoned.

BACKGROUND OF THE INVENTION

1. Field of the Invention

The present invention relates to a dry immunoassay element in which a homogeneous enzyme immunoassay is utilized, and an immunoassaying process in which the dry immunoassay element is used.

2. Description of the Prior Art

Analyses of the constituents of the living body or plasma proteins or the like contained in the body fluids, such as, blood and urine, are useful for diagnosing the condition of diseases or judging the course of curing, and thus they occupy important parts in the field of clinical test. The so-called enzyme immunoassay has been known in the art as one method for analyzing such constituents (ligands) generally present in a small amount in the body fluids. The enzyme immunoassay may be classified into heterogeneous systems for which band/free (B/F) separation must be effected, and homogeneous system for which B/F separation is not necessary. The reactions in the homogeneous system are based on the phenomenon that the enzymatic activity of the labelling enzyme is affected by some interference caused by binding of an antibody to the antigen (ligand), and the inhibition due to antigen-antibody binding is generally utilized. It is believed that enzymatic activity is suppressed by a steric hindrance caused by binding the enzyme to the substrate or a change in three-dimensional structure of the enzyme, when the antibody which is generally a large molecule is bound to the antigen in the enzyme-labelled antigen.

A dry analysis method is known, in which a homogeneous enzyme immunological reaction is utilized (see Unexamined Japanese Patent Publication No. 80050/1986). This dry analysis method uses the following reagent composition:

(A) A water-insoluble high polymer substrate labelled with a dye; and (B) A conjugate of an antibody against the ligand and an enzyme for the substrate.

A sample containing an antigen (ligand) is allowed to react with a predetermined amount of an enzymelabelled antibody for a predetermined time to form a complex of the antigen and enzyme-labelled antibody, and then a water-insoluble and dye-labelled high polymer substrate is added to the reaction mixture to initiate an enzymatic reaction.

The enzyme of the enzyme-labelled antibody which has not been bound with the antigen reacts with the water-insoluble high polymer substrate to produce a lower molecular weight dye-labelled product which is soluble in water. On the other hand, the complex of macromolecular antigen, antibody and enzyme cannot exhibit the enzymatic activity towards the high polymer substrate. Accordingly, as the quantity of the antigen in the sample is increased, the product produced by the enzymatic reaction decreases. The quantity of the lower molecular weight product is determined by measuring the optical density of the absorption produced by the colored moiety and the antigen in the sample is analyzed quantitatively.

However, in this method, since a high polymer substrate bound to a dye, such as a dye-starch, is used and the dye bound to amylose which is the decomposition product formed by the action of the enzyme (amylase) is determined, the high polymer substrate and the reaction product must be separated prior to the measurement or determination. This is problematic because complicated operations are required which prevent automation of the analysis system. On the other hand, in the routine clinical test wherein a number of test samples must be processed, the samples must be analyzed rapidly using a simple process preferably by automated operations. For this reason, dry analysis elements have been proposed (see, for example, Unexamined Japanese Patent Publication Nos. 53888/1974, corresponding to U.S. Pat. No. 3,992,158, 77356/1984, corresponding to EP 0097 952A and 102388/1974 and U.S. Pat. No. 4,459,358).

However, in this known analysis element, since a high polymer substrate bound to a dye, such as, a dye-starch, is used and the dye bound to amylose which is the decomposition product formed by the action of the enzyme (amylase) is determined, the high polymer substrate and the reaction product must be separated prior to the measurement or determination. It is, therefore, necessary to provide a light-shielding layer containing, for example, titanium dioxide fine particles between the reagent layer containing the unreacted substrate and the detection layer for receiving the reaction product. An analysis element having this laminated structure is not preferred because it to take too much time for the soluble reaction product formed in the reagent layer to be diffused through the light-shielding layer into the detection layer. As a result, a rapid quantitative determination, which is a major advantage of the dry analysis element, cannot be carried out.

It is possible to improve the diffusibility of the reaction product by introducing a hydrophilic group, such as, a carboxyl or sulfo group, into the substrate to accelerate the diffusion of the reaction product. However, sites for introduction of such substituting groups are limited. Also, the introduction of the group may lower the molecular extinction coefficient of the dye site governing the sensitivity of the analysis.

SUMMARY OF THE INVENTION

One object of this invention is to provide an immunoassay element utilizing a homogeneous enzyme immuno-assay for enabling the rapid analysis of an analyte at high sensitivity using a simple operation.

We have discovered that this can be achieved by use of an immunoassay element for quantitatively analyzing a macromolecular (high polymer) antigen by determining the change in enzymatic activity caused by a reaction between said macromolecular antigen and an enzyme-labelled antibody, said element comprising a substrate layer containing a non-diffusible substrate which forms a diffusible material in the presence of said enzyme, and a reagent layer containing a decomposing enzyme for further decomposing said diffusible material into a lower molecular weight product. The enzyme-labelled antibody may be contained in the substrate layer or in another layer laminated on the substrate layer.

Another object of this invention is to provide a process for quantitatively analyzing an analyte while using the aforementioned immunoassay element.

This object may be achieved by determining the change in enzymatic activity caused by a reaction between the macromolecular antigen and an enzyme-labelled antibody, comprising the steps of:

(a) applying said sample on a substrate layer containing a non-diffusible substrate to form a diffusible material in the presence of said enzyme;

(b) allowing the diffusible material to migrate into a reagent layer containing a decomposing enzyme for decomposing the diffusible material into a lower molecular weight product; and (c) measuring the amount of the lower molecular weight product formed in the reagent layer.

The enzymatic activity of the enzyme of the enzyme-labelled antibody, bound to the macromolecular antigen contained in the sample, towards the non-diffusible substrate is inhibited by steric hindrance. As a result, the quantity of the diffusible material formed in the substrate layer is inversely proportional to the quantity of the antigen contained in the sample. The diffusible material formed in the substrate layer migrates rapidly into the reagent layer, where it is further decomposed into a lower molecular weight product. The lower molecular weight product may be detected in a detection layer. The unreacted non-diffusible substrate is held in the substrate layer.

DESCRIPTION OF THE PREFERRED EMBODIMENTS

Layer Construction of Immunoassay Element

Figure 1:
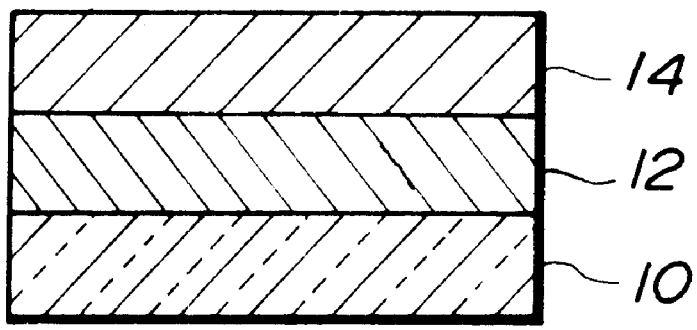
FIG. 1 is an illustration showing the layer structure of the immunoassay element according to this invention.

FIG. 1 shows an embodiment of the immunoassay element according to this invention. In this Figure, reference numeral 10 designates a transparent support on which are laminated reagent layer 12 and a substrate layer 14. The substrate layer 14 is composed of a water-permeable material and contains a non-diffusible substrate for a labelling enzyme which forms a conjugate with the antibody. This substrate forms a diffusible material in an amount inversely proportional to the quantity of the macromolecular antigen which is determined quantitatively by the enzymatic activity of the enzyme-labelled antibody.

The reagent layer 12 is composed of a water-permeable material and contains a decomposing enzyme. The decomposing enzyme decomposes the diffusible material, which diffuses or migrates from the substrate layer into a lower molecular weight product. The reagent layer 12 further contains a reagent composition for detecting the thus fragmented lower molecular weight product.

Analyte (Substance to Be Analyzed)

The substance to be analyzed by the present invention is a macromolecular antigen having a high molecular weight and an antigenic determinant. In the analysis element of this invention, the interfering or suppressing function of the conjugation of the macromolecular antigen and the enzyme-labelled antibody is utilized. Accordingly, it is preferable that the macromolecular antigen has a relatively high molecular weight so as to maximize its influence on the enzymatic activity. For instance, the inventive analysis element exhibits its advantages when used for the analysis of an antigen having a molecular weight of not less than about 20,000 daltons, and preferably not less than about 50,000 daltons.

Any high polymer, having sufficiently high molecular weight may be analyzed by the analysis element of the invention, so long as they act as antigens against the antibodies which can be prepared and contained in the analysis element. Examples of the antigens which may be analyzed by the use of the analysis element of this invention include hormones secreted from various endocrine glands, plasma proteins, such as, immunoglobulin, albumin, ferritin and C-reactive proteins (hereinafter referred to as CRP), viruses, such as, HB antigen, bacteria, and antigens present in various organs, blood and urine, such as, protein and α-fetoprotein and carcinoembryonic antigen (CEA).

The sample containing the macromolecular antigen is not limited and many kinds of sample may be analyzed by this invention; typical examples including blood (whole blood, blood plasma, or blood serum), lymph fluid and urine. It is preferred to preclude suspended particles, such as, blood cells, when such particles are present. However, a sample may be directly spotted on the analysis element of this invention without precluding such suspended particles when the analysis element has a filter layer, according to a preferred embodiment of this invention.

Antibody

The antibody labelled with an enzyme is a specific antibody against the macromolecular antigen which is the analyte. The antibody may be obtained by conventional processes, and a monoclonal antibody may be preferably used to improve the sensitivity. The antibody may be a papain fragment, such as, $F(ab')_2$, Fab' or Fab.

Labelling Enzyme, Non-diffusible Substrate and Fragmenting Enzyme

The enzyme bound to the antibody as a label decomposes the non-diffusible high polymer substrate to produce a diffusible product, which may be fragmented or decomposed to a yet lower molecular weight product by the action of the fragmenting enzyme.

The non-diffusible substrate is not dispersible into the aqueous sample liquid and not diffusible into the reagent layer by itself.

The fragmenting enzyme is contained in the re-agent layer and converts the diffusible product produced from the non-diffusible substrate by the action of the label enzyme bound to the antibody to form into a detectable lower molecular product. Suitable combinations of enzyme and substrate may be selected to provide easy detection.

Labelling Enzyme

Examples of suitable labeling enzymes include hydrolases which form diffusible oligomers from non-diffusible substrates composed of polymers, a specific example is glucosidase. Examples of glucosidase are α-amylase, β-amylase and dextranase. Other usable hydrolases are cellulase, collagenase, mannase, lipase and ribonuclease.

The method for linking the enzyme to the antibody may be selected considering the functional groups of both reactants. Utilizable functional groups include, for example, amino, carboxyl, hydroxyl, thiol, imidazole, and phenyl. For example, amino groups may be linked to each other by a number of known methods, such as, the isocyanate method, glutaraldehyde method, difluorobenzene method and benzoquinone methods. An amino group may be linked to a carboxyl group by a method in which the carboxyl group is converted to succinylimide ester, or by other methods including the carbodiimide method, Woodward reagent method and the periodic acid oxidation method (Nakane method) in which the amino group is linked with a sugar chain. When a thiol group is utilized, one of the carboxyl groups is converted to succinylimide ester which is reacted with cysteine to introduce a thiol group and then both groups are linked to each other using a bifunctional linking reagent which reacts with the thiol group. The methods in which the phenyl group is utilized include the diazotization method and the alkylation method. The linking method is not limited to the aforementioned methods, and may be selected from the methods described in "Method in Immunology and Immunochemistry", vol. 1, (C. A. Williams, M. W. Chase, Academic Press (1967)) or "KOSO MEN'EKI SOKUTEI-HO" (Enzyme Immunoassay), edited by Ishikawa, Kawai and Miyai, Igaku Shoin, 1978. The enzyme may be linked to the antibody at any desired ratio. After the completion of the linking reaction, the reaction product is refined by the gel filtration or ion exchange chromatography, and may be dried by the lyophilizing process as desired.

It is preferred that the enzyme is not affected by any hindering factor present in the sample, and that a competitive enzyme of the same kind is not present in the sample. However, when an enzyme which is the same as the labelling enzyme is present in the sample, an enzyme inhibitor may be used. The enzyme inhibitor may be one which inhibits the enzyme in the sample to a greater extent than the inhibiting activity towards the labelling enzyme. It is most preferable that the enzyme inhibitor entirely inactivates the enzyme in the sample and does not deactivate the labelling enzyme. However, in practical use, it suffices that the blank value is not raised at the determination step and the enzyme inhibitor may be inactivated to restore the activity of the enzyme in the sample after the completion of the determination. It also suffices if the enzyme inhibitor does not inhibit the enzyme in the enzyme-la-belled antibody, but can inhibit the activity of free enzyme. The enzyme inhibitor may be selected from known enzyme inhibitors so that the selected enzyme has the specific characteristics as aforementioned. Otherwise, an antibody against the enzyme which contained in a sample to cause a problem is prepared and used as an enzyme inhibitor.

Non-Diffusible Substrate

Examples of the substrate for said α-amylase, β-amylase or dextranase are carboxymethylated starch, starch, amylose or amylopectin.

Fragmenting Enzyme

The fragmenting enzyme may be an enzyme of the same kind as of the labelling enzyme. In such a case, it is preferred that the labelling enzyme is an endo-active enzyme which fragments the molecule intramolecularly to produce an oligomer, and the fragmenting enzyme is exoactive and acts at the terminal of the molecule to produce a monomer. For instance, when the non-diffusible substrate is a polymer, e.g. starch, a fragmenting enzyme for decomposing the diffusible oligomer, e.g., maltose, produced by the action of the labelling enzyme, to a monomer, e.g., glucose, is used. Examples of fragmenting enzymes include hydrolases for saccharides. Specific examples include α-amylase, β-amylase, dextranase, glucoamylase and α-glucosidase.

When carboxymethyl cellulose is used as the non-diffusible substrate and cellulase is used as the labelling enzyme, C1 enzyme may be used as the fragmenting enzyme. Likewise, when the combination of galactane and galactanase is used, β-galactosidase may be used as the fragmenting enzyme; and when the combination of RNA and ribonuclease is used, exoribonuclease may be used as the fragmenting enzyme.

The combination of the labelling enzyme, the non-diffusible substrate and the fragmenting enzyme may be selected from the enzymes and substrates described in known publications, for example, "Enzyme Handbook" (Bunji Maruo and Nobuo Tamiya, Asakura Shoten, 1982); and "Biochemical Handbook" (Nobumasa Imura et al., Maruzen, 1984).

The lower molecular weight product produced by fragmentation in the reagent layer by the action of the fragmenting enzyme may be optically detected by using a known detection reagent.

Any known methods may be employed for detecting the glucose formed by the action of the aforementioned fragmenting enzyme. Examples include a method in which hydrogen peroxide formed by the oxidation of glucose in the presence of glucose oxidase is detected, e.g., the method wherein a Trinder reagent is used, as described in Ann. Clin. Biochem., 6, 24 (1964) and J. Clin. Pathol., 22, 246 (1969), the method wherein a Trinder reagent is used, as described in Unexamined Japanese Patent Publication No. 50991/1974 (corresponding to U.S. Pat. No. 3,886,045), U.S. Pat. No. 3,992,158 and Unexamined Japanese Patent Publication No. 164356/1980 (corresponding to U.S. Pat. No. 4,292,272), the method wherein a reagent containing a triaryl-substituted imidazole leuco dye is used, as described in Unexamined Japanese Patent Publication No. 26188/1978 (corresponding to U.S. Pat. No. 4,089,747) and Unexamined Japanese Patent Publication No. 45557/1983 (Chemical Abstracts, 99, (1983):209284j), the method wherein a reagent containing an imidazole leuco dye substituted with a diarylmonoaralkyl, as described in Unexamined Japanese Patent Publication Nos. 193352/1984 (corresponding to EP 0122641A) and 224677/1985 (corresponding to U.S. Pat. No. 4,665,023)), a method wherein NADH produced in the presence of glucose dehydrogenase and NAD is detected, and a method wherein glucose-6-phosphate produced in the presence of hexokinase is detected. Among these detection methods, the most preferred is the method wherein glucose is oxidized in the presence of glucose oxidase to form hydrogen peroxide which is detected using peroxidase and a leuco dye because of its high detection sensitivity.

These detection reagents may be contained in the reagent layer together with the fragmenting enzyme, or may be contained in another layer disposed below the reagent layer, for example, in a second reagent layer or a detection layer to detect the lower molecular weight product produced. When a leuco dye is used, it is preferred that the dye is dispersed in the hydrophilic binder in the solution in a water-immiscible solvent in consideration of the stability of the formed dye.

Layer Structure of the Analysis Element

The dry immunoassay element of this invention may have a layer structure similar to those of various dry analysis elements. The element may be of a multi-layered construction including, in addition to the substrate layer and the reagent layer, a support, a spreading layer, a detection layer, a light-shielding layer, an adhesive layer, a water-absorbing layer, an undercoating layer and so on. Examples of such analysis elements are disclosed in the specifications of Unexamined Japanese Patent Publication Nos. 53888/1974 (corresponding to U.S. Pat. No. No. 3,992,158), 40191/1976 (corresponding to U.S. Pat. No. 4,042,353) and 164356/1980 (corresponding to U.S. Pat. No. 4,292,272).

When a light-transmitting and water-impermeable support is used, a dry immunoassay element having the following construction may be used, although the present invention is not limited to any of the following constructions:

(1) a reagent layer disposed on a support, and a substrate layer superposed on the reagent layer;
(2) a support, a detection layer, a reagent layer and a substrate layer superposed in this order;
(3) a support, a detection layer, a reagent layer and a substrate layer superposed in this order;
(4) a support, a reagent layer, a light-reflecting layer and a substrate layer superposed in this order;
(5) a support, a detection layer, a reagent layer, a light-reflecting layer and a substrate layer superposed in this order;
(6) a support, a detection layer, a light-reflecting layer, a reagent layer and a substrate layer superposed in this order;
(7) a support, a second reagent layer, a light-reflecting layer, a first reagent layer and a substrate layer superposed in this order; and
(8) a support, a detection layer, a second reagent layer, a light-reflecting layer, a first reagent layer and a substrate layer superposed in this order.

In the constructions (1) to (6), the reagent layer may be composed of plural layers. The reagent layer may be an immunological reaction layer which contains a component capable of taking part in a immunological reaction, as will be described hereinafter.

A water-absorbing layer may be disposed between the support and the reagent or detection layer. Filtering layers may be interposed between the adjacent layers. A spreading layer may be disposed on the substrate layer, or the substrate layer may act also as a spreading layer.

Substrate Layer

The substrate layer 14 is composed of a water-permeable layer and contains a non-diffusible substrate which is a substrate for the enzyme labelling the antibody.

In order to ensure water-permeability of the substrate layer, it is preferable that the substrate layer is composed of a porous medium or a layer composed of a hydrophilic polymer binder.

The porous layer may be fibrous or non-fibrous. As the fibrous material, filter paper, non-woven cloth, woven cloth, e.g., plain woven cloth, knitted cloth, e.g., tricot knitted cloth, or filter paper made of glass fibers ay be used. Examples of the non-fibrous material include a membrane filter composed of cellulose acetate described in Unexamined Japanese Patent Publication No. 53888/1974 (corresponding to U.S. Pat. No. 3,992,158), and a particulate structure layer containing interconnected voids and composed of inorganic or organic fine particles as disclosed in Unexamined Japanese Patent Publication Nos. 90859/1980 (corresponding to U.S. Pat. No. 4,258,001) and 70163/1983 (corresponding to U.S. Pat. No. 4,486,537). A laminated structure made of partially bonded multiple porous layers may also be preferably used, examples of such structure being disclosed in Unexamined Japanese Patent Publication Nos. 4549/1986 (corresponding to EP 0166365A), 116258/1987 (Chemical Abstracts, 108 (1988):3041y), 138756/1987 (EP 0226465A), 138757/1987 (EP 0226465A) and 138758/1987 (EP 0226465A).

The porous layer may be a spreading layer having a so-called metering function to spread a liquid over an area substantially in proportion to the volume of the liquid fed. Preferable materials for the spreading layer are woven and knitted fabrics. The woven fabrics or the like may be subjected to a glow discharge treatment as described in Unexamined Japanese Patent Publication No. 66359/1982 (corresponding to GB 2.087.074A and U.S. Pat. No. 4,783, 315). In order to adjust the area or rate of spreading, the spreading layer may contain a hydrophilic polymer or a surfactant as described in Unexamined Japanese Patent publication Nos. 222770/1985 (corresponding to EP 0162301A), 219397/1988 (corresponding to DE 37 17 913A), 112999/1988 (corresponding to DE 37 17 913A), and 182652/1987 (corresponding to DE 37 17 913A).

One convenient method is wherein the substrate is impregnated into or coated on a porous membrane made of, for example, paper, cloth or a high polymer, and then the composite is applied on another water-permeable layer, for example, a reagent layer superposed on the support by a method as described in Unexamined Japanese Patent publication No. 164356/1980 (corresponding to U.S. Patent 4,292,272). A further method comprises the steps of bonding a porous layer on another water-permeable layer, for example, a reagent layer, by a method as described above, and coating a composition containing the substrate on the porous layer. Any known methods may be employed for the impregnation or coating on the porous layer. Coating may be effected by selecting a suitable method, for example, dip coating, doctor coating, hopper coating and curtain coating.

Although the thickness of the substrate layer made by any of the aforementioned methods is not limited, the thickness may range within 1 $\mu$m to 50 $\mu$m, and preferably, from 2 $\mu$m to 30 $\mu$m, when the layer is provided as a coating layer. When it is provided by another method, for example by piling of a laminate, the thickness thereof may be varied within a wide range of from several tens of $\mu$m to several hundreds of $\mu$m.

The substrate layer may be a water-permeable layer composed of a hydrophilic polymer binder, such as, gelatin and derivatives thereof, e.g., phthalated gelatin, derivatives of cellulose, e.g., hydroxyethyl cellulose, agarose, sodium alginate, acrylamide copolymers, methacrylamide copolymers, copolymers of acryl amides or methacrylamides with various vinyl monomers, polyhydroxyethyl methacrylate, polyvinyl alcohol, polyvinyl pyrrolidone, sodium polyacrylate, and copolymers of acrylic acid with various vinyl monomers.

A substrate layer composed of a hydrophilic polymer binder may be provided by coating an aqueous solution or dispersion of the substrate, an additional reagent composition and a hydrophilic polymer binder on another layer, such as, a support or a detection layer, and then drying the coated solution or dispersion, as disclosed in the specifications of Japanese Patent Publication No. 21677/1988 (corresponding to U.S. Pat. No. 3,992,158), Unexamined Japanese Patent publication Nos. 164356/1980 (corresponding to U.S. Pat. No. 4,292,272), 101398/1979 (corresponding to U.S. Pat. No. 4,132,528), and 292063/1986 (Chemical Abstracts, 106, 210567y). The thickness of the dried substrate layer containing a hydrophilic polymer as the binder may range from about 2 $\mu$m to about 50 $\mu$m, and preferably, from about 4 $\mu$m to about 30 µm, and the coverage thereof may range from about 2 g/m² to about 50 g/m², and preferably, from about 4 g/m² to about 30 g/m².

To improve the characteristics, such as, coating characteristics, diffusibility of the diffusible material, reactivity and storage stability, the substrate layer may include, in addition to the non-diffusible substrate, various organic or inorganic additives, for example, enzyme activators, coenzymes, surfactants, pH buffer composition, fine particles, antioxidants, etc. Examples of buffer systems which may be contained in the substrate layer, may include pH buffer compositions, as described in "KAGAKU BINRAN, KISOHEN", edited by Japanese Chemical Society (MARUZEN, Tokyo, 1966), pp.1312–1320; R. M. C. Dawson et al., "Data for Biological Research", 2nd Edition (Oxford at the Clarendon Press, 1969), pp.476–508; "Biochemistry", 5, pp. 467–477 (1966); and "Analytical Biochemistry", 104, pp. 300–310 (1980). Specific examples of usable buffers are buffer compositions containing tris (hydroxymethyl)-amino-methane (Tris), buffer compositions containing phosphates, buffer compositions containing borates, buffer compositions containing citric acid or citrates, buffer compositions containing glycine, buffer reagents containing Bicine, and buffer reagents containing HEPES.

Reagent Layer

The reagent layer 12 contains a fragmenting enzyme and may contain a detection reagent composition for detecting the lower molecular weight product formed by the action of the fragmenting enzyme as desired.

The reagent layer is composed of a water-permeable layer which is preferably a continuous (non-porous) layer made of a hydrophilic polymer binder, similar to the water-permeable layers as described in the description of the substrate layer. The hydrophilic polymer binder may be selected based on the diffusible product formed in the substrate layer and the coloring reagent contained in the reagent layer.

Support

The support 10 may be light-non-transmitting (opaque), light-semi-transmitting (translucent) or light-transmitting (transparent), and it is generally preferable that the support is light-transmitting and water-impermeable.

Preferable materials for the light-transmitting and water-impermeable support are polyethylene terephthalate and polystyrene. In general, an undercoating is provided or the support is subjected to a hydrophilization treatment in order to firmly adhere the hydrophilic layer.

Immunological Reaction Layer

The substrate layer 14 shown in FIG. 1 may contain an enzyme-labelled antibody, in addition to the non-diffusible substrate, to form an immunological reaction layer in which an immunological reaction takes place. With such a construction, a homogeneous enzyme immunological reaction takes place in the element only by spotting a sample on the element.

Alternatively, the enzyme-labelled antibody may be contained in a separate layer.

Figure 2:
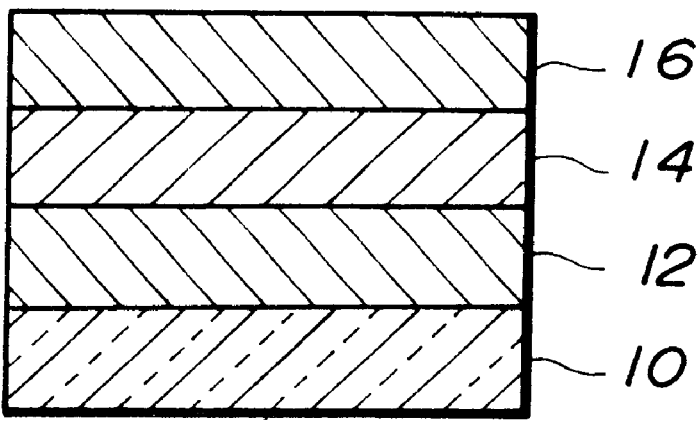
FIG. 2 is an illustration showing another embodiment of the immunoassay element according to this invention.

For example, as shown in FIG. 2, a water-permeable layer 16 containing the enzyme-labelled antibody may be disposed on the substrate layer 14 to form the immunoassay element of the invention. In this case, the macromolecular antigen binds with the antibody of the enzymelabelled antibody contained in the layer 16, and then migrates into the substrate layer 14.

In order to contain an enzyme-labelled antibody in a separate layer in the substantially dry state or in the substantial absence of water, the enzyme-labelled antibody may be dissolved or dispersed in a non-aqueous medium, such as, an alcohol, e.g., ethanol and then the solution or dispersion is impregnated in the water-permeable layer.

Process for Preparing the Immunoassay Element

The dry immunoassay element of the invention may be prepared by any of the known processes described in the specifications of aforequoted patents.

The analysis element of the invention may be cut into a square piece having sides each ranging from about 15 mm to about 30 mm or a disc having substantially the same area. It is preferred, in view of the preparation, packaging, shipping, storage and measuring operations, that the element be contained in a slide frame as disclosed, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent Publication No. 63452/1982, Unexamined Japanese Utility Model Publication No. 32350/1983 and Unexamined Japanese Patent Publication No. 501144/1983 (corresponding to International Publication WO 83/00391) for use as a slide for chemical analysis. For convenience in some uses, it may be formed in a tape shape which is contained in a cassette or magazine, or a small piece thereof may be applied on or contained in a card having an opening.

Analyzing Method Using the Immunoassay Element

The analysis element of the invention may be used for the quantitative analysis of an analyte ligand in a sample liquid by using it through the operations described in the specification of the aforequoted patents.

For example, about 5 µl to about 30 µl, preferably 8 µl to 15 µl, of an aqueous sample liquid, such as, serum, plasma or urine, is spotted or otherwise fed on the substrate layer 14. The analysis element spotted with the sample liquid is then incubated at a constant temperature of from about 20° C. to about 45° C., preferably at a constant temperature of from about 30° C. to about 40° C., for 1 to 10 minutes. The reflection optical density of the color or the change in color in the element may be measured from the light-transmitting support side, and the quantity of the ligand contained in the sample can be determined using a preliminarily prepared calibration curve based on the principle of colorimetry. The volume of the spotted liquid sample and the time and temperature for incubation are maintained constant to improve the accuracy in quantitative analysis.

The measuring operation may be carried out while using the chemical analysis apparatus described in Unexamined Japanese Patent Publication Nos. 125543/1985, 220862/1985, 294367/1986 and 161867/1983 (the last-mentioned Publication corresponding to U.S. Pat. No. 4,424, 191) to realize a quantitative analysis at a high accuracy by extremely easy operations.

Meantime, a semi-quantitative analysis may be conducted by judging the degree of coloring by naked eye if such visual judgment is adequate for the object or required accuracy.

When the analysis element does not contain the enzyme-labelled antibody, the aqueous sample liquid is mixed with a solution containing the enzyme-labelled anti-body to complete the binding reaction, and then spotted on the substrate layer.

SYNTHESIS EXAMPLE (1) Synthesis of Enzyme-Labelled Antibody a) Preparation of CHM Amylase:

5 mg of Bacillus subtilis a-amylase was dissolved in 1 ml of a 0.1 M glycerophosphate (pH 6.3), and 100 µl of a 200 mg/ml solution of [4-(maleimidomethyl)cyclohexane-1-carboxylic acid] succinimide ester (CHMS) in DMF was added thereto and allowed to react at room temperature for an hour. The reaction mixture was introduced into a Sephadex G-25 column and a 0.1 M glycerophosphate (pH 6.3) solution was passed through the column to provide an eluted fraction containing 4-(maleimidomethyl)cyclohexane-1-carboxyamido α-amylase (CHM amylase).

b) Preparation of Anti-CRP Mouse IgG F(ab')$_2$

300 µg of papain was added to 10 mg of anti-CRP mouse IgG (in 2 ml of 0.1 M acetate buffer (pH 5.5)), and stirred at 37° C. for 18 hours. A 0.1 N NaOH solution was added to the reaction liquid to adjust the pH value thereof to pH 6.0. The liquid was then introduced into a AcA-44 gel column preliminarily equilibrated with a 0.1 M phosphate buffer (pH 6.3) containing 1 mM EDTA, followed by elution with the aforementioned phosphate buffer solution. The peak portion of the eluate having molecular weights of approximately 100,000 was collected and concentrated to 1 ml to obtain the objective anti-CRP mouse IgG F(ab')$_2$.

c) Preparation of Bound of α-Amylase-Anti-CRP Mouse IgG Fab'

100 µl of a 10 mg/ml aqueous solution of 2-mercaptoethylamine HCl salt was added to 1 ml of a 0.1 M phosphate buffer (containing 1 mM EDTA, pH 6.0) containing 6 mg of the anti-CRP mouse IgG F(ab')$_2$ prepared in step b) and stirred at 37° C. for 90 minutes. The reaction mixture was subjected to gel filtration by a Sephadex G-25 column which was preliminarily equilibrated with a 0.1 M phosphate buffer (pH 6.3) to remove unreacted 2-mercaptoethylamine to obtain HS-Fab'. 2 mg of the CHM a-amylase prepared by the step a) were added to HS-Fab' to react at 37° C. for 90 minutes. The reaction mixture was then subjected to gel filtration using the AcA-34 column equilibrated with a 0.1 M phosphate buffered 5 mM calcium chloride solution (pH 7.0) to collect a fraction having molecular weights of not less than 200,000, and the fraction was concentrated to obtain the objective conjugate of α-amylase and anti-CRP mouse IgG Fab'.

EXAMPLE 1

A reagent solution containing a cross-linking reagent was coated onto a colorless and transparent poly-ethylene terephthalate (PET) sheet (support) coated with a gelatin undercoating and having a thickness of 180 µm. The sheet was then dried, forming a reagent layer wherein the respective components had the coverages as set forth below.

| | |
|---|---|
| Alkaline-treated Gelatin | 14.5 g/m$^2$ |
| Nonylphenoxypolyethoxyethanol (Containing 9 to 10 (average) of Oxyethylene Units) | 0.2 g/m$^2$ |
| Glucose oxidase | 5,000 U/m$^2$ |
| Peroxidase | 15,000 U/m$^2$ |
| Glucoamylase | 5,000 U/m$^2$ |
| 2-(4-hydroxy-3,5-dimethoxyphenyl)-4-[4-(dimethylamino)phenyl]-5-phenethyl-imidazole (Leuco Dye) Acetate | 0.38 g/m$^2$ |
| Bis[(vinylsulfonylmethylcarbonyl)amino]-methane | 0.1 g/m$^2$ |

An adhesive layer was coated onto the reagent layer to have the following coverage, and then dried.

| | |
|---|---|
| Alkaline-treated Gelatin | 14.5 g/m$^2$ |
| Bis[(vinylsulfonylmethylcarbonyl)amino]-methane | 0.1 g/m$^2$ |

Then, an aqueous solution containing the following reagent was coated over the surface of the adhesive layer to have the following coverage to swell the gelatin layer and a tricot knitted cloth made by knitting PET spun yarn of 36 gage corresponding to 50 deniers and having a thickness of about 250 µm was then laminated thereon, by pressing with a uniform light pressure to form a porous spreading layer.

| | |
|---|---|
| Nonylphenoxypolyethoxyethanol (Containing 9 to 10 (average) of Oxyethylene Units) | 0.15 g/m$^2$ |
| Bis[(vinylsulfonylmethylcarbonyl)amino]-methane | 0.4 g/m$^2$ |

Thereafter, a substrate layer was formed by coating a substrate, followed by drying, to have the following coverages, to prepare the multi-layered analysis element for the quantitative analysis of CRP.

| | |
|---|---|
| Carboxymethyl Starch | 4 g/m$^2$ |
| Nonylphenoxypolyethoxyethanol (Containing 9 to 10 (average) of Oxyethylene Units) | 0.2 g/m$^2$ |

The thus prepared element was cut into 1.5 cm squares, and each square was placed in a slide frame described in Unexamined Japanese Patent Publication No. 63452/1982 to prepare a multi-layered dry slide 1 for the analysis of CRP.

Figure 3:
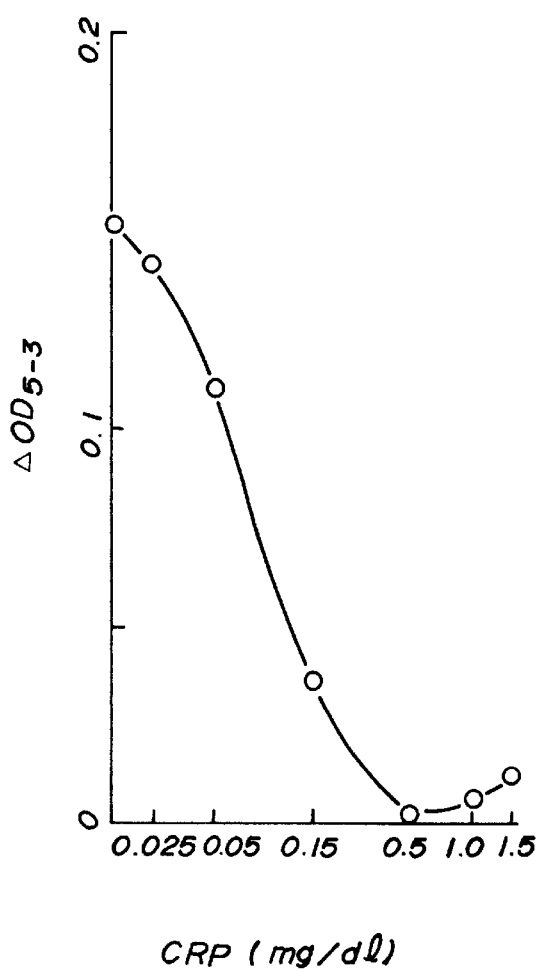
FIG. 3 is a graphic representation showing a calibration curve when the immunoassay element of Example 1 is used.

Test for Appraisal of the Properties 0.1 mg/ml for each of the amylase-anti-CRP IgG conjugate prepared by Synthesis Example (1) was added to a 50 mM glycerophosphate buffer (pH 7) containing a predetermined quantity of CRP and incubated at 37° C. for 20 minutes. 10 µl of each solution was spotted on slide 1. Slide 1 was maintained at 37° C., and the optical density of the reflected light having a wavelength of 650 nm was measured from the support side. The difference in optical density ($\Delta OD_{5-3}$) of the reflected lights measured respectively after the lapse of 3 minutes and 5 minutes is shown in FIG. 3.

EXAMPLE 2

A multi-layered analysis element having a tricot knitted cloth layer was prepared in the same manner as in Example 1. On the tricot knitted cloth layer, which served both as a substrate layer and a spreading layer, a solution of the amylase-anti-CRP IgG conjugate (Synthesis Example (1)) in ethanol was coated and dried to provide a coverage of 3 mg/m², to prepare a multi-layered immunoassay slide 2 for the analysis of CRP.

Test for Appraisal of the Properties

Figure 4:
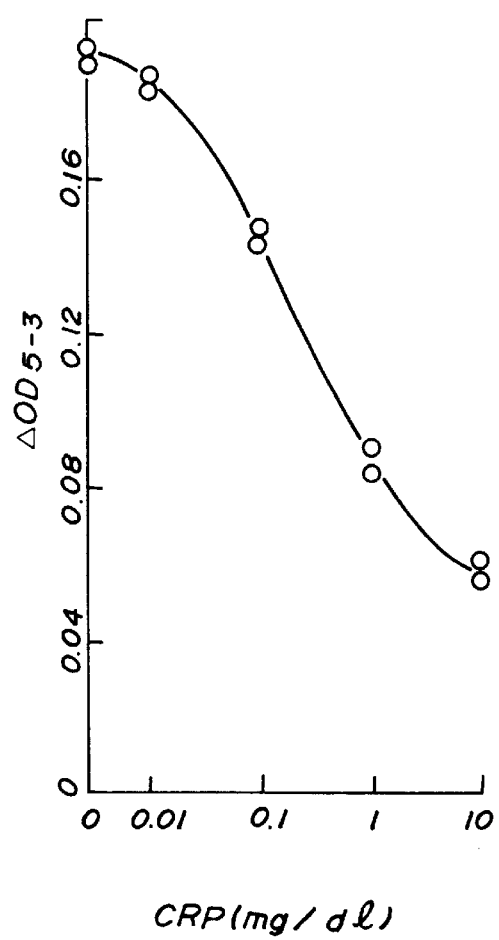
FIG. 4 is a graphic representation showing the calibration curve when the immunoassay element of Example 2 is used.

10 μl of a 50 mM glycerophosphate buffer solution (pH 7) containing a known quantity of CRP was spotted on slide 2. Slide 2 was maintained at 37° C., and the optical density of the reflected light having a wavelength of 650 nm was measured from the PET support side. FIG. 4 shows the difference in optical density ($\Delta OD_{5-3}$) between the optical density of the reflected light measured after the lapse of 3 minutes from spotting and the optical density of the reflected light measured after the lapse of 5 minutes from spotting. It should be appreciated from the calibration curve shown in FIG. 4 that the dry immunoassay element for the analysis of CRP, prepared in accordance with the present invention, can be used for quantitative analysis of CRP to give accurate results.

What is claimed is:

1. An immunoassay element for quantitatively analyzing an amount of a macromolecular antigen in a sample by determining the change in enzymatic activity of a labelling enzyme caused by a reaction between
   1) the macromolecular antigen, and
   2) an antibody which can react and bind specifically with the macromolecular antigen and which is labelled with the labelling enzyme; said element comprising:
      (a) a substrate layer containing a non-diffusible substrate composed of a polymer which is capable of being digested by the labelling enzyme into a diffusible oligomer which migrates from the substrate layer; and
      (b) a reagent layer containing a digesting enzyme for further digesting the diffusible oligomer, which has migrated from said substrate layer, into a detectable monomer;
   wherein the labelling enzyme is an endo-active hydrolase capable of digesting the polymer into the diffusible oligomer and the digesting enzyme is an exo-active hydrolase which digests the diffusible oligomer into the detectable monomer.

2. The immunoassay element of claim 1, wherein the antibody is contained in said substrate layer or a layer superposed on said substrate layer.

3. The immunoassay element of claim 1, wherein the non-diffusible substrate is a polysaccharide, the labelling enzyme is an endo-active glucosidase, and the digesting enzyme is an exo-active glucosidase.

4. The immunoassay element of claim 3, wherein the non-diffusible substrate is a polysaccharide which is a polymer composed of glucose units;
   wherein the labelling enzyme is endo-active glucosidase which digests the polysaccharide to produce an oligomer of the glucose units;
   wherein the digesting enzyme is an exo-active glucosidase which digests the oligomer to produce a monomer of the glucose; and
   wherein the detectable monomer is glucose monomer.

5. The immunoassay element of claim 1, wherein the reagent layer contains a reagent composition which reacts with the detectable mononer to form a dye having an absorption peak in the visible wavelength range.

6. The immunoassay element of claim 5, wherein the reagent composition reacts with the detectable mononer to form a peroxide.

7. The immunoassay element of claim 6, wherein the reagent composition contains a leuco dye which colors upon oxidation.

8. The immunoassay element of claim 7, wherein said reagent layer contains a hydrophilic binder, and wherein the reagent composition contains a dispersion of a solution of leuco dye in a water-insoluble solvent in the hydrophilic binder.

9. The immunoassay element of claim 7, wherein the reagent composition contains glucose oxidase, a peroxidase and a leuco dye.

10. The immunoassay element of claim 1, which further comprises a water-permeable layer which contains a reagent composition which reacts with the detectable mononer to form a dye having an absorption peak in the visible wavelength range.

11. The immunoassay element of claim 10, wherein the reagent composition reacts with the detectable mononer to form a peroxide.

12. The immunoassay element of claim 11, wherein the reagent composition contains a leuco dye which colors upon oxidation.

13. The immunoassay element of claim 1, wherein the macromolecular antigen has a molecular weight of not less than about 20,000 daltons.

14. The immunoassay element of claim 13, wherein the macromolecular antigen has a molecular weight of not less than about 50,000 daltons.

15. The immunoassay element of claim 13, wherein the macromolecular antigen is a protein.

16. The immunoassay element of claim 1, wherein said substrate layer is composed of fibrous material and said reagent layer is composed of hydrophilic polymer binder.

17. The immunoassay element of claim 16, wherein said fibrous material is selected from the group consisting of a woven cloth and a knitted cloth.

18. An immunoassay process for quantitatively analyzing an amount of a macromolecular antigen in a sample by determining the change in enzymatic activity of a labelling enzyme caused by a reaction between
   1) the macromolecular antigen, and
   2) an antibody which can react and bind specifically with the macromolecular antigen and which is labelled with the labelling enzyme; said process comprising the steps of:
      (a) applying the sample, which has previously been mixed with said antibody to complete said reaction, onto the substrate layer of the element of claim 1, and
      (b) measuring the amount of the detectable monomer formed in the reagent layer.

19. The method of claim 18, wherein measuring step (b) is carried out calorimetrically.

20. The immunoassay process of claim 18, wherein said substrate layer is composed of fibrous material and said reagent layer is composed of a hydrophilic polymer binder.

21. The immunoassay process of claim 20, wherein said fibrous material is selected from the group consisting of a woven cloth and a knitted cloth.

22. An immunoassay process for quantitatively analyzing an amount of a macromolecular antigen in a sample by determining the change in enzymatic activity of a labelling enzyme caused by a reaction between
   1) the macromolecular antigen, and
   2) an antibody which can react and bind specifically with the macromolecular antigen and which is labelled with the labelling enzyme; said process comprising the steps of:

(a) applying the sample, which has previously been mixed with said antibody to complete said reaction, on a substrate layer containing a non-diffusible substrate composed of a polymer for forming a diffusible oligomer which migrates from the substrate layer in the presence of the labelling enzyme;

(b) allowing the diffusible oligomer formed in the substrate layer to migrate into a reagent layer containing a digesting enzyme for further fragmenting the diffusible oligomer into a detectable monomer; and (c) measuring the amount of the detectable monomer formed in the reagent layer;

wherein the labelling enzyme is an endo-active hydrolase which digests the polymer into the diffusible oligomer and the digesting enzyme is an exo-active hydrolase which digests said diffusible oligomer into said detectable monomer.

23. The immunoassay process of claim 22, wherein said substrate layer is composed of fibrous material and said reagent layer is composed of a hydrophilic polymer binder.

24. The immunoassay process of claim 23, wherein said fibrous material is selected from the group consisting of a woven cloth and a knitted cloth.

* * * * *